(12) United States Patent
Kalies

(10) Patent No.: US 8,744,868 B2
(45) Date of Patent: Jun. 3, 2014

(54) METHOD FOR STORING AND REPORTING PHARMACY DATA

(75) Inventor: Ralph F. Kalies, Picket, WI (US)

(73) Assignee: Omnicare, Inc., Covington, KY (US)

( * ) Notice: Subject to any disclaimer, the term of this patent is extended or adjusted under 35 U.S.C. 154(b) by 4046 days.

(21) Appl. No.: 10/681,954

(22) Filed: Oct. 8, 2003
(Under 37 CFR 1.47)

(65) Prior Publication Data
US 2004/0148195 A1 Jul. 29, 2004

Related U.S. Application Data

(60) Provisional application No. 60/417,056, filed on Oct. 8, 2002.

(51) Int. Cl.
*G06Q 50/24* (2012.01)
(52) U.S. Cl.
USPC .................................... 705/2; 705/3
(58) Field of Classification Search
USPC ...................................... 705/1, 2–3
See application file for complete search history.

(56) References Cited

U.S. PATENT DOCUMENTS

| | | | |
|---|---|---|---|
| 5,189,608 A | 2/1993 | Lyons et al. | 364/408 |
| 5,832,449 A | 11/1998 | Cunningham | |
| 5,845,255 A | 12/1998 | Mayaud | |
| 5,924,074 A | 7/1999 | Evans | 705/3 |
| 6,128,602 A | 10/2000 | Northington et al. | 705/35 |
| 6,138,121 A | 10/2000 | Costa et al. | 707/100 |
| 6,234,964 B1 | 5/2001 | Iliff | |
| 6,322,502 B1 | 11/2001 | Schoenberg et al. | 600/300 |
| 6,341,286 B1 | 1/2002 | Kawano | 707/101 |
| 6,347,329 B1 | 2/2002 | Evans | 709/202 |
| 6,363,393 B1 | 3/2002 | Ribitzky | 707/102 |
| 6,463,417 B1 * | 10/2002 | Schoenberg | 705/2 |
| 6,609,115 B1 * | 8/2003 | Mehring et al. | 705/51 |
| 7,346,655 B2 * | 3/2008 | Donoho et al. | 709/204 |
| 7,398,217 B2 * | 7/2008 | Lewis et al. | 705/2 |
| 7,401,027 B2 * | 7/2008 | Moore et al. | 705/2 |
| 2001/0041991 A1 | 11/2001 | Segal et al. | 705/3 |
| 2002/0016923 A1 | 2/2002 | Knaus et al. | 713/200 |
| 2002/0026332 A1 | 2/2002 | Snowden et al. | 705/3 |
| 2002/0046346 A1 | 4/2002 | Evans | 713/200 |
| 2002/0049727 A1 | 4/2002 | Rothkopf | 707/1 |
| 2002/0103903 A1 | 8/2002 | Bruton, III et al. | 709/225 |

(Continued)

*Primary Examiner* — Valerie Lubin
*Assistant Examiner* — Reginald R Reyes
(74) *Attorney, Agent, or Firm* — Ostrolenk Faber LLP

(57) ABSTRACT

A method is disclosed for gathering, processing, storing and reporting pharmacy data. Data from individual pharmacies is transmitted regularly to a data repository via an electronic communications network. Upon receipt at the data repository, the data first must pass through an access security screen wherein data failing to meet predetermined criteria are rejected. If the data are determined to be valid, it is added to a data warehouse database by a computer data server. Authorized users may issue requests to the data repository based on current and/or historical data. Such requests may be made at any time via the electronic communications network to create reports based on current data. The user first sends a request to the data repository for access. Once access to the data repository is granted, the user is able to obtain various types of information residing within the data warehouse. The amount and types of data available to the user may be limited by the user's predetermined security level clearance and need-to-know, in order to protect patient privacy. The data may be presented to the user in a variety of predetermined report formats, as established by the type of data and the function of the user.

11 Claims, 5 Drawing Sheets

(56) References Cited

U.S. PATENT DOCUMENTS

| | | | |
|---|---|---|---|
| 2002/0111833 A1 | 8/2002 | Dick | 705/3 |
| 2002/0116227 A1 | 8/2002 | Dick | 705/3 |
| 2002/0116509 A1 | 8/2002 | DeLaHuerga | 709/229 |
| 2002/0120573 A1 | 8/2002 | McCormick | 705/50 |
| 2002/0154628 A1 | 10/2002 | Akasaka et al. | 370/352 |
| 2002/0165736 A1 | 11/2002 | Tolle et al. | 705/3 |
| 2002/0177758 A1 | 11/2002 | Schoenberg et al. | 600/300 |
| 2002/0177759 A1 | 11/2002 | Schoenberg et al. | 600/300 |
| 2002/0178031 A1 | 11/2002 | Sorensen et al. | 705/2 |
| 2002/0188476 A1 | 12/2002 | Bienvenu et al. | 705/3 |

* cited by examiner

METHOD FOR STORING AND REPORTING PHARMACY DATA

This application claims priority to U.S. Provisional Patent Application 60/417,056, filed Oct. 8, 2002, the contents of which are hereby incorporated by reference.

FIELD

This invention relates to a method for managing pharmacy data. Specifically, the invention relates to a method for accumulating, storing and using pharmacy data using an electronic network as a communications and data transfer medium.

BACKGROUND

Many business organizations today operate from multiple locations. Indeed, some companies have sites worldwide. Getting accurate information in a timely manner to the right people in such an organization can be a difficult, if not a nearly impossible, task. Manually prepared and mailed reports are untimely, require substantial time and resources, and may be of limited use in situations where large amounts of data are continually accumulated and analyzed. Further, access to up-to-date information can be critical in the decision-making process where success, failure, and profitability may all be tied to the timing of the decision.

In addition, various personnel within an organization have differing information needs. For example, healthcare personnel may need to review the medical aspects of pharmaceutical transactions whereas a business manager may only need to review the financial aspects of the transactions. This creates a need for customized reports having formatting to suit the particular needs of each user. Further, some information is sensitive from a business or patient privacy perspective and must be secured, with access being limited to predetermined personnel.

A critical characteristic of data is "freshness." In situations where large quantities of data are continually generated, it is important that the latest information be available to support an analysis or decision by management. Relying upon only a limited quantity of data, or data collected for only a limited period of time, may present a false or misleading view of a changing or trending metric.

Most managed care organizations (MCOs) offer a pharmacy benefit to their members as part of a healthcare package. The pharmacy benefit is administered by the MCO, or in many cases, by a prescription benefits manager (PBM) that has contracted with the MCO to manage its pharmacy benefit program. PBMs offer a variety of services, such as: establishing pharmacy networks (also known as publicly-held corporate pharmacies, or "PCPs"), claims processing, report generation, generic drug substitution, formulary development and management, academic detailing, maintenance drug programs, mail-order pharmacies, negotiating pharmaceutical manufacturer rebates, drug utilization evaluation ("DUE"), and disease management and outcomes assessment.

Pharmacies within a Managed Care Organization ("MCO") are an example of information-driven organizations that require near "real-time" access to data in order to operate most effectively. MCOs work to minimize costs through a variety of means, including volume purchases, quality control, and negotiated healthcare fees. As such, there is a high level of interest in electronically acquiring and utilizing as much historical and ongoing data as possible regarding drug use and benefit, comparative costs of alternate therapies, and patient demographics. This information may be collected, organized and stored in a data storage medium, often referred to as a "data warehouse." A data warehouse is an electronic database wherein large quantities of related data from many operational systems are merged into a single database, to provide an integrated information view based on logical queries of the data. A properly maintained data warehouse is a valuable tool that can provide information for use in a wide variety of therapeutic, statistical and economic analyses to aid the MCO medical and business staffs in making well-informed healthcare and business related decisions. The data warehouse can also provide feedback regarding the impact of prior decisions and protocols, which may facilitate improvements in patient outcomes and operational efficiency, and thus reduce the cost of medical care.

Methods of transferring electronic data, such as dial-in modems, have a number of limitations. For example, a data repository utilizing modems typically requires many telephone lines to support the input and output needs of multiple data sources and data users. Economic considerations demand that a limited number of lines be made available, creating a "bottleneck" for data flow in and out of the repository. In addition, the data transmission rate is often limited by modem and/or telephone line capability, increasing the amount of time required for data transfer. The internet's worldwide accessibility and capability of rapidly transferring data to and from a large number of locations overcome many of the limitations of dial-in modems, making it the medium of choice for multi-site operations. However, the internet's open and accessible architecture makes it a significant security risk. It is not uncommon for sensitive data transmitted via the internet to be accessed by unauthorized personnel. This can result in tampering of data or the dissemination of sensitive or competitive information.

Thus, there is a need for a method to efficiently accumulate pharmacy data, verify its validity, store it, and make it available in a useful format on a secured basis to authorized personnel. There is also a need to prevent unauthorized users from tampering with or viewing the data.

SUMMARY

The present invention overcomes the aforementioned limitations of present methods for gathering and reporting pharmacy data by providing a repository for receiving pharmacy data, the data being electronically transmitted to the repository directly by pharmacies that generate the data. Specifically, data from individual pharmacies within an MCO or pharmacy benefits management organization are prepared and formatted in accordance with predetermined protocols and standards. The data are timely transmitted to a data repository comprising a data warehouse, via an electronic communications network. Upon receipt at the data repository, the data first must pass through an access security screen. If the data are faulty, such as being in an improper format, it is rejected and a notification is sent to the submitter of the data. If the data are determined to be valid, it is added to the data warehouse database by a data server. Authorized personnel within the MCO or pharmacy benefits management organization may then issue requests to the data repository for reports based on current and/or historical data. Such requests may be made at any time via the electronic communications network.

To generate reports the requestor first sends a request to the data repository for access. The data repository may include access security measures requiring that the user provide credentials such as a user name and/or password in order to obtain the requested report. Once access to the data repository is granted, the requestor is able to obtain various types of information residing within the data warehouse by using logical queries and/or selecting among predetermined report formats. The amount and types of data available to the requestor may be limited by the requestor's predetermined security level clearance and need to know, in order to protect business-sensitive information and patient privacy. The data may be presented to the requestor in a variety of predetermined report formats, as established by the type of data and the function of the requester.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

Figure 1:
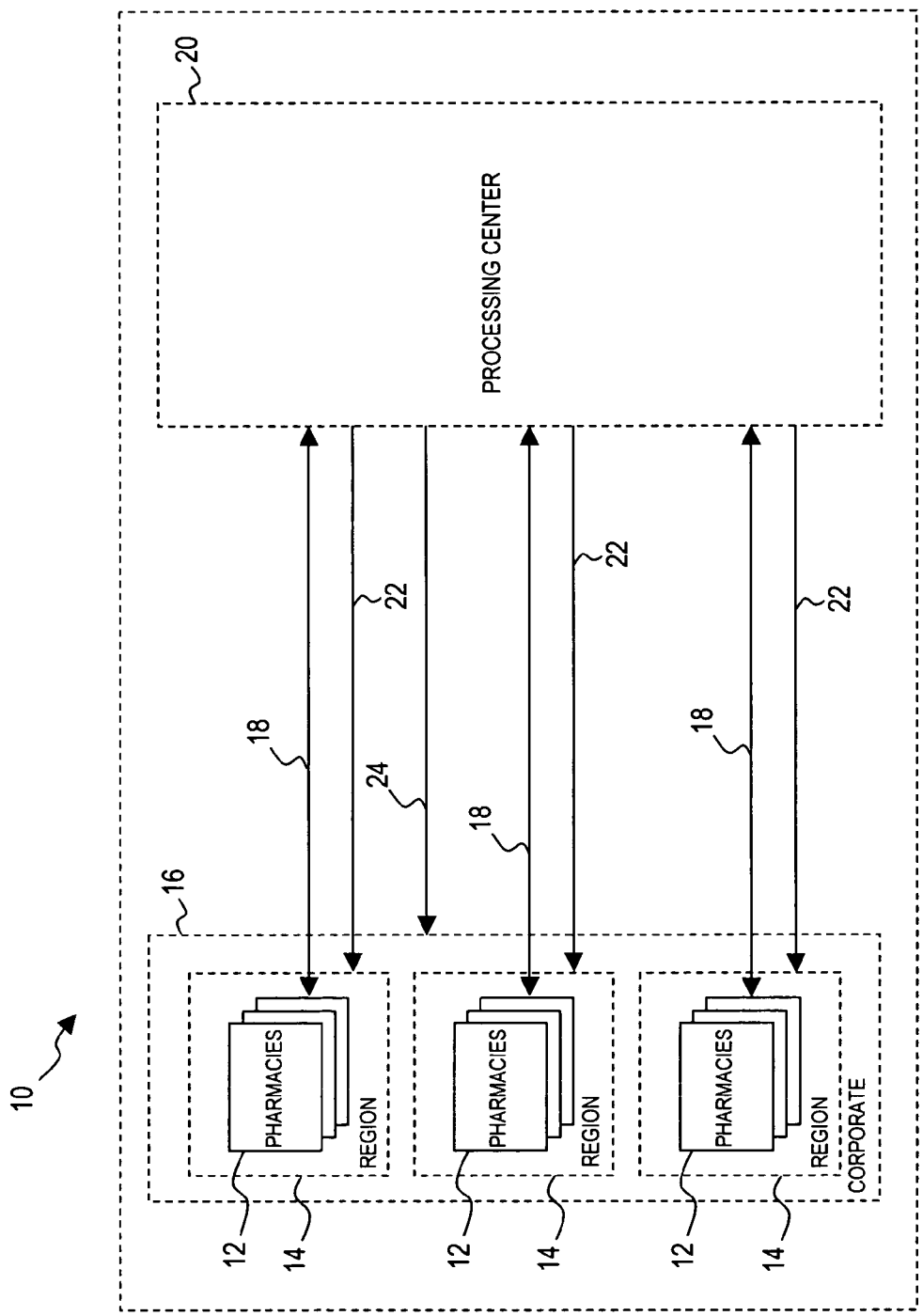
FIG. 1 illustrates the general flow of information between a hierarchical corporate pharmacy and a data processing center according to an embodiment of the present invention.

A schematic diagram of the general organization of an example pharmacy system 10 is shown in FIG. 1. The system 10 may be comprised of a number of commonly-owned or related pharmacies 12 which are arranged into a hierarchy of regions 14. One skilled in the art will recognize that the term "regions" may refer to geographic regions, organizational regions, logically structured regions or any combination thereof. The regions 14 may in turn be organized under a corporate 16 umbrella. The pharmacy organization 10 further includes a processing center 20 for handling the various administrative aspects of the organization.

With continued reference to FIG. 1, arrows 18, 22, 24 indicate the typical flow of information for the system 10 with regard to pharmacy-related data. The pharmacies 12 act as a source of pharmacy data for processing center 20, as indicated by arrows 18. Pharmacy data may comprise patient demographic information, transaction records, and prescription information. The pharmacies 12 may also obtain from processing center 20 various reports pertaining to pharmacy records and transactions, including patient-specific medical information (such as drug utilization) and business reports (such as financial performance.) The reports flow from processing center 20 to the pharmacies 12, likewise indicated by arrows 18.

A variety of other users may also obtain reports from processing center 20 based on the pharmacy data. At the regional level 14 of pharmacy system 10 the data flows from processing center 20 to personnel at the regional level, as indicated by arrows 22. Personnel within a region 14 include regional managers, who may draw upon the pharmacy data to obtain reports pertaining to metrics for the various pharmacies within their region. Topics covered by a regional-level report include, but are not limited to: financial performance, quality-control, customer-service performance, and regulatory compliance. A regional-level report may focus on a single pharmacy within a region 14, a sub-set of pharmacies 12 within the region, or all pharmacies within the region. Corporate 16 personnel may obtain reports for individual pharmacies 12, or for the regions 14 within the corporation, as indicated by arrow 24. Corporate-level reports may provide information relating to financial performance, quality-control, customer-service performance, and regulatory compliance. Reports at corporate 16 level may focus on one or more pharmacies 12 within a region 14, or one or more regions, subsets of pharmacies and regions, and aggregates of all pharmacies and/or regions.

Figure 2:
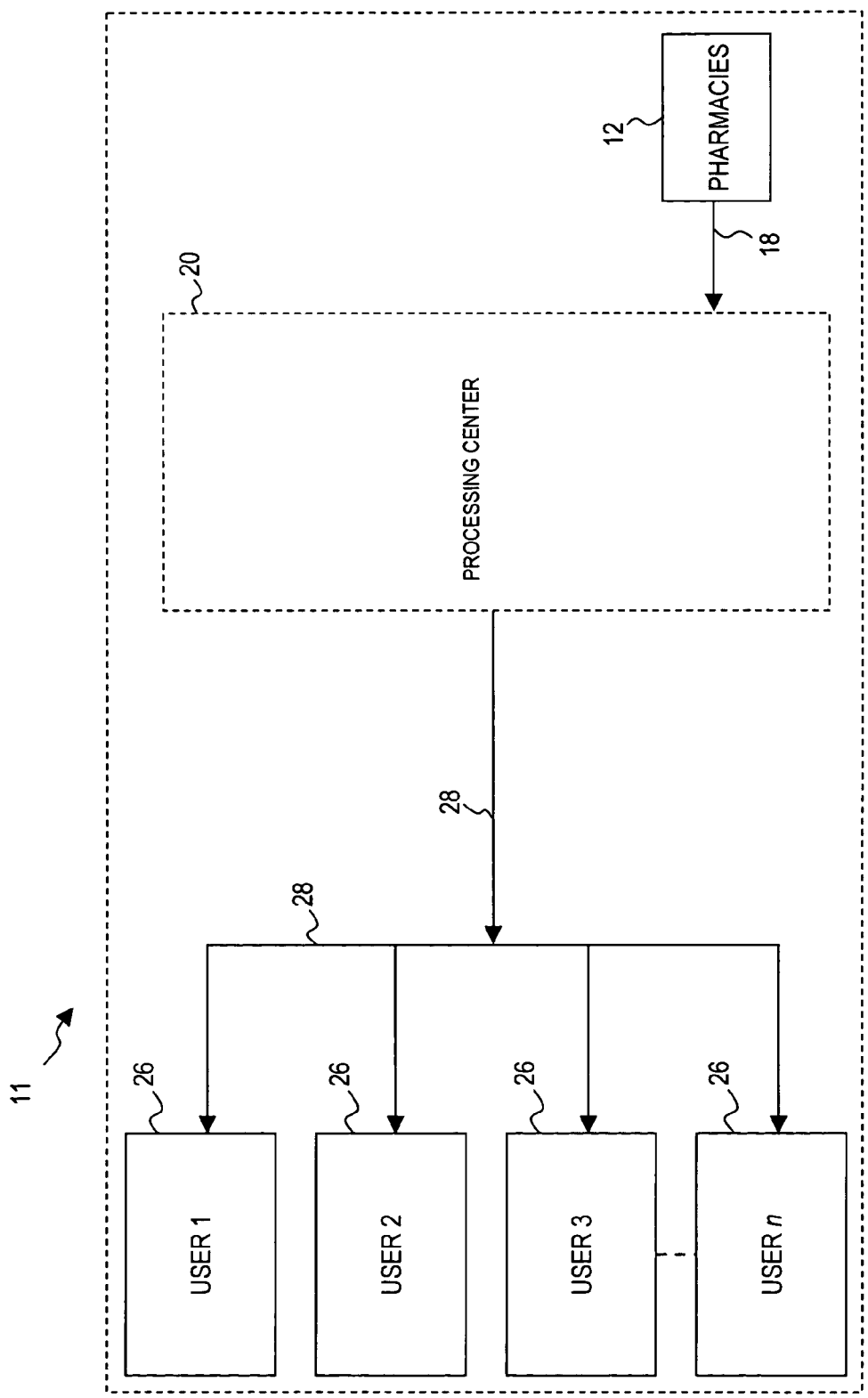
FIG. 2 depicts the general flow of information between a non-hierarchical organization and a data processing center according to an alternate embodiment of the present invention.

The flow of information of an organization 11 according to an alternate embodiment of the present invention is shown in FIG. 2. One or more pharmacies 12 act as a source for pharmacy data for a processing center 20, as indicated by arrow 18. One or more non-hierarchical users 26 within organization 11 may obtain various reports from processing center 20, as indicated by arrow 28. Users 26 may comprise any administrative or management personnel within organization 11 having a need for the reports and/or data. However, the users 26 need not be hierarchically aligned. Indeed, users 26 need not even interact with each other. For example, User 1 may need financial information, while User 2 is interested in only regulatory compliance data and User 3 desires transaction data for supply and purchasing purposes. The pharmacies 12 may also function as users 26 of data to obtain various reports from processing center 20 based on the pharmacy data. In this embodiment the types of reports and the amount of data available are established in accordance with a predetermined set of criteria, such as the job function and the need-to-know of each user 26.

Figure 3:
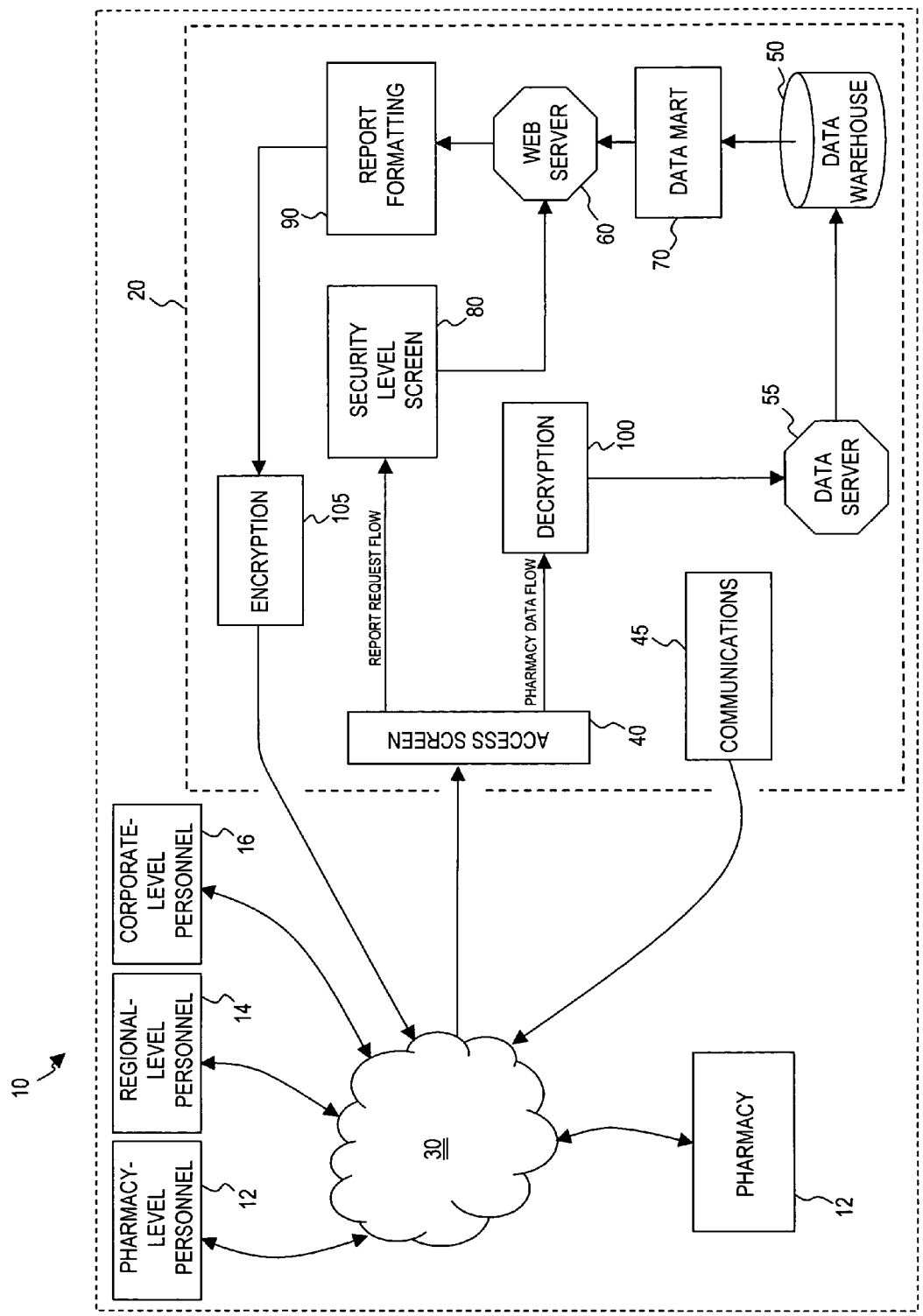
FIG. 3 is a flow diagram of a method for accumulating, processing, storing, and reporting pharmacy data according to the embodiment of FIG. 1.

A flow diagram depicting the general arrangement of a method for storing and reporting pharmacy data in accordance with an embodiment of the present invention is shown in FIG. 3. One or more pharmacies 12 within an MCO or other pharmacy system 10 transmit medical, financial, and other information related to pharmaceutical transactions to a processing center 20. The pharmacy data are preferably transmitted via an electronic communications network 30. Reports based on the stored pharmacy data may be requested by hierarchical personnel at the pharmacy 12 level, regional 14 level and corporate 16 level.

Figure 4:
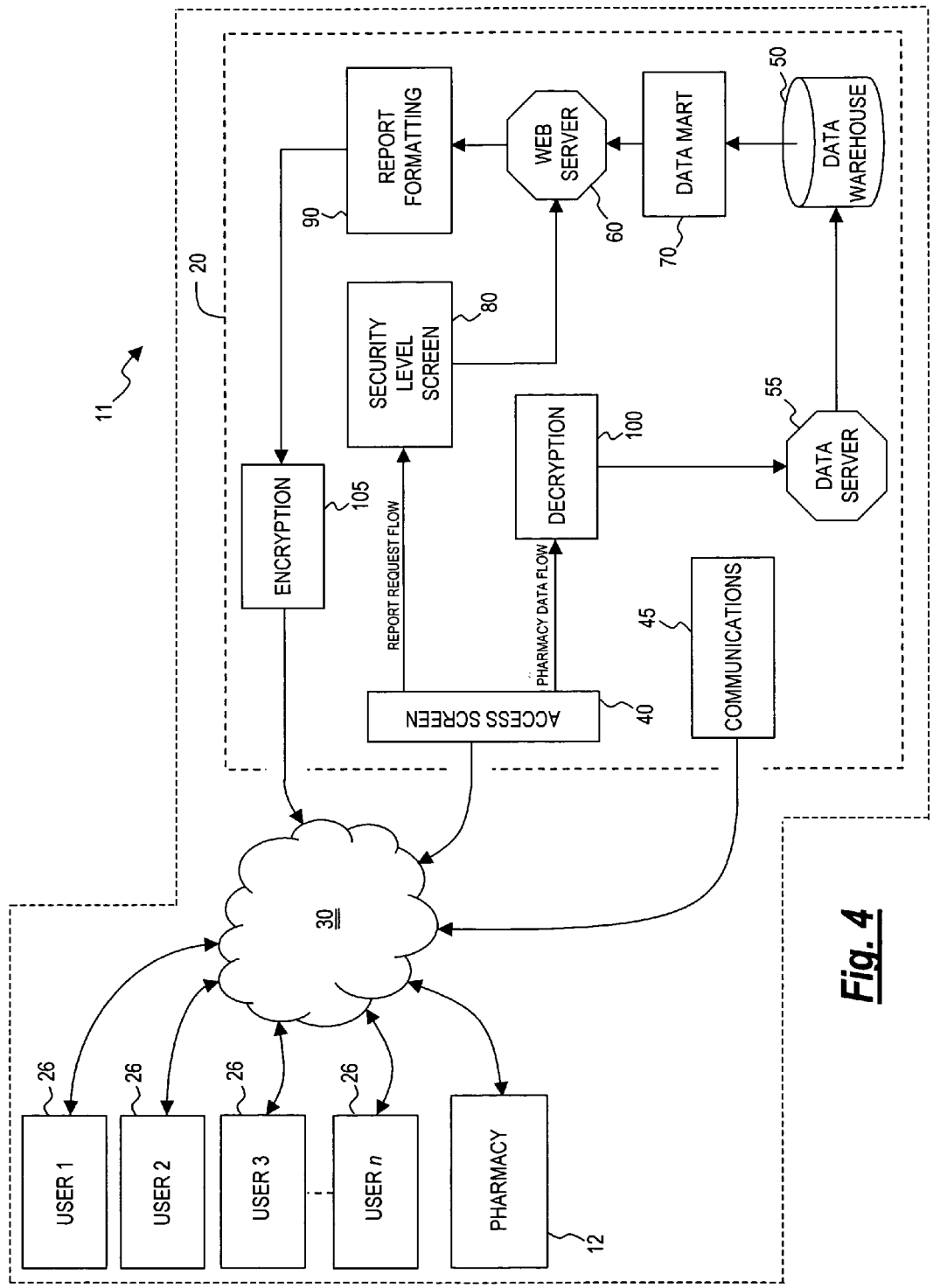
FIG. 4 is a flow diagram of a method for accumulating, processing, storing, and reporting pharmacy data according to the embodiment of FIG. 2.

A flow diagram depicting the general arrangement of a method for storing and reporting pharmacy data in accordance with an alternate embodiment of the present invention is shown in FIG. 4. One or more pharmacies 12 within an MCO or other organization 11 transmit medical, financial, and other information related to pharmaceutical transactions to a processing center 20. The pharmacy data are preferably transmitted via an electronic communications network 30. Reports based on the stored pharmacy data may be requested by non-hierarchical personnel 26.

The following discussion of electronic communications network 30, and of the functional components of processing center 20 relating to the inflow of data, is equally applicable to the embodiments of FIG. 3 and FIG. 4 unless otherwise noted.

Electronic communications network 30 may be any conventional network that facilitates electronic communications between remotely-situated computers, such as an intranet, wide-area network ("WAN") or the internet. Electronic communications network 30 may optionally include one or more means of protecting the data in order to ensure patient privacy and to prevent data tampering and alteration. Protection means include, but are not limited to, firewalls and virtual private networks ("VPNs"), as is known by those skilled in the art.

Processing center 20 is an organizational portion of the pharmacy organizations 10, 11 that is adapted to obtain, organize and store pharmacy data. Pharmacy data obtained from the various pharmacies 12 is used for such purposes as billing, financial performance, medical reviews, and performance evaluations. Functional components of processing center 20 may include an access security screen 40, a communications portion 45, a data warehouse 50, a data server 55, a web server 60, a data mart 70, security level access screen 80, a report generation portion 90, a data decryption means 100, and a data encryption means 105.

A pharmacy 12 desiring to transfer data to processing center 20 may be required to present certain credentials to the processing center in order to effect the data transfer. This function is handled by access security screen 40. The access restriction function of access security screen 40 may be accomplished by any conventional means, such as predetermined usernames, passwords, and secured websites. The level of security may be enhanced by conventional "anti-hacking" methodologies, such as encrypted passwords, case-sensitive passwords, passwords requiring pseudorandom combinations of numbers and letters, and limiting the number of access attempts. If proper credentials are not presented, data transfer is not enabled and the submitting pharmacy 12 may be notified of the rejection via a communications portion 45. Communications portion 45 may comprise any conventional means of communication, such as letters, faxes, telephone, courier and telex, although electronic notification via network 30 is preferable. If a proper username and/or password are received for the purpose of transferring data from pharmacy 12 to processing center 20, access security screen 40 may optionally review or check any incoming data before accepting the transfer. Example data checks include validation of the data source, a data format validity check, and an optional check for computer "viruses." If the data are unacceptable, the transfer is rejected and the pharmacy 12 submitting the data is notified of the rejection via communications portion 45. If the data are deemed acceptable by access security screen 40, pharmacy 12 may likewise be notified of the acceptance of the data by communications portion 45. Accepted data may be forwarded to an optional data decryption portion 100 prior to storage, as discussed in detail below.

In another embodiment of the present invention, the pharmacy data may be encrypted prior to transmission by pharmacy 12 in order to protect patient privacy and/or prevent tampering of data. In this embodiment, encrypted data accepted by access screen 40 is decrypted at 100 to restore the data to a usable form prior to storing it. Any conventional computer data encryption/decryption method may be used for data decryption portion 100, such as asymmetric key-based algorithms wherein one electronic code or "key" is used to encrypt data and a different key is used to decrypt the same data. Symmetric key-based algorithms, or block-and-stream ciphers may also be used. Using these cipher types, the data are separated into portions, and those portions are encrypted and decrypted based on a specific key. Stream ciphers may also be used, wherein the portions are encrypted on a bit-by-bit basis.

Data server 55 is a conventional computer server system, such as a file server, disk server, or database server. Data server 55 is adapted such that it is in electronic communication with access screen 40 and/or decryption portion 100 to receive accepted data. Data server 55 is in further electronic communication with data warehouse 50 such that the data server can forward the accepted data to the data warehouse for storage.

Data warehouse 50 is a data repository for organizing, structuring and storing pharmacy data. A data warehouse is a process by which large quantities of related data from many operational systems is merged into a single, standard repository to provide an integrated information view based on logical queries. Types of logical queries may relate to "data mining," which can be defined as a process of data selection, exploration and building models using vast data stores to uncover previously unknown patterns. Other queries may be in support of research on a particular subject. Data warehouse 50 is a valuable tool that can provide information for use in a wide variety of therapeutic, statistical, and economic analyses and interventions to aid the PCP and healthcare organizations in making healthcare and business related decisions. Data warehouse 50 can also provide feedback regarding the impact of prior decisions, facilitating improvements in patient care, operational efficiency, and reducing the cost of medical care.

The data stored in data warehouse 50 may optionally be de-identified in any conventional manner to achieve compliance with any applicable patient privacy regulations, such as those found in the U.S. Health Insurance Portability and Accountability Act ("HIPAA") or in other Acts which may be later legislated and/or adopted. In particular, 45 C.F.R. Parts 160 and 164 of the Act relate to standards for the privacy of individually-identifiable health information (the "Privacy Rule"), promulgated by the Department of Health and Human Services (HHS). In part the Privacy Rule can restrict the acquisition and use of certain types of patient data, particularly patient-identifiable health information. It should be noted that "de-identifying" patient data can entail more than merely redacting the patient's name. This is due to the fact that other patient information such as demographics, medical information, and healthcare facility information could be used separately or in combination to discern the identity of some patients. De-identification thus may involve the deletion or alteration of some portion of patient data to protect patient privacy, while preserving the overall statistical and analytical integrity of the data.

The following discussion of the functional components of processing center 20, relating to the outflow of data from the processing center, is equally applicable to the embodiments of FIG. 3 and FIG. 4 unless otherwise noted.

In addition to controlling the inflow of data as previously discussed, access security screen 40 may also screen requests for data extraction from processing center 20. In the embodiment of FIG. 3, access to the data is preferably limited to a predetermined hierarchical group of personnel, such as personnel at corporate pharmacies 12, personnel at the regional 14 level and corporate 16 level personnel. In the non-hierarchical embodiment of FIG. 4, access may be limited to a predetermined group of users 26. The portion of access security screen 40 pertaining to restricting access to the data stored within processing center 20 may be accomplished by any conventional means, such as predetermined usernames, passwords, and secured websites. The level of security may be enhanced by conventional "anti-hacking" methodologies, such as encrypted passwords, case-sensitive passwords, passwords requiring pseudorandom combinations of numbers and letters, and limiting the number of access attempts.

Security level screening function 80 serves to protect medical and business information by making reports and data selectively available to users according to a predetermined arrangement. In the hierarchical embodiment of FIG. 3, the pharmacies 12 may obtain reports that are pertinent to their operation, via the electronic communications network 30. However, each pharmacy 12 may be restricted or prevented from accessing information regarding other pharmacies in the network. At the regional 14 pharmacy group level, administrative and management personnel may, for example, obtain business performance reports via electronic communications network 30 for each pharmacy 12 within the regional pharmacy group and conduct comparative analyses between them. However, each regional 14 group may be restricted or prevented from accessing data for pharmacies outside of their own region. At the corporate 16 level, administrative and management personnel may, for example, obtain via the electronic communications network 30 a variety of reports pertaining to all levels of pharmacy system 10, such as individual pharmacies 12, comparisons between pharmacies, performance of regional 14 pharmacy groups, comparisons between regional pharmacy groups, and overall performance of the corporate 16 pharmacy network. In the non-hierarchical embodiment of FIG. 4, the types of reports and the level of detail are predetermined according to a set of criteria, such as the job function and the need-to-know of each user 26 within organization 11.

Personnel at levels 12, 14, 16 of FIG. 3 and users 26 of FIG. 4 may be collectively termed "requesters" herein for convenience. If the reports and/or data requested are outside the requestor's predetermined scope of access privileges, security level screen 80 rejects the request. The requester may accordingly be notified via communications portion 45 that the request could not be processed.

In yet another embodiment of the present invention, the choices of reports and/or data presented to the requestor for selection may vary with the privileges of the requester. In this embodiment the display of choices presented to a requestor on a computer display (not shown) includes only choices within the particular requestor's scope of privileges.

If the reports and/or data requested by a particular requestor are within the scope of the requestor's authority, the request is forwarded to a web server 60. Web server 60 is a conventional computer server system, such as a file server, disk server, or database server. Web server 60 is adapted such that it is in electronic communication with security level screen 80 to receive approved requests for reports and/or data. Web server 60 is in further electronic communication with a data mart 70 such that web server 60 can receive stored data from data warehouse 50. Lastly, web server 60 is in electrical communication with a report formatting portion 90, the web server being adapted to retrieve data from data warehouse 50 and/or data mart 70 and send it to the formatting portion.

At least a portion of the report and/or data used to fulfill a request may reside in data mart 70. Data mart 70 is a repository of data derived from data warehouse 50 and is designed to handle requests for reports and/or data based on the pharmacy data. Data mart 70 is adapted to meet the specific demands of a particular group users in terms of analysis, content, presentation, and ease-of-use by storing a portion of the larger set of data residing in data warehouse 50 for the particular purpose of providing data for a predetermined set of reports pertinent to a particular requestor or group of requestors.

Report formatting portion 90 receives raw data from data warehouse 50 and/or data mart 70 via web server 60 and places the data in a predetermined format to facilitate ease of review of the data by the requestor. The predetermined format may vary depending on the type of data received, but is preferably a standard format for the data type selected to aid readability and minimize confusion.

The formatted report is then prepared for transmission to the requestor. The report may optionally be encrypted at 105 to protect privacy using any of the conventional encryption/decryption methods previously discussed. The report is then sent to the requestor via network 30.

Figure 5:
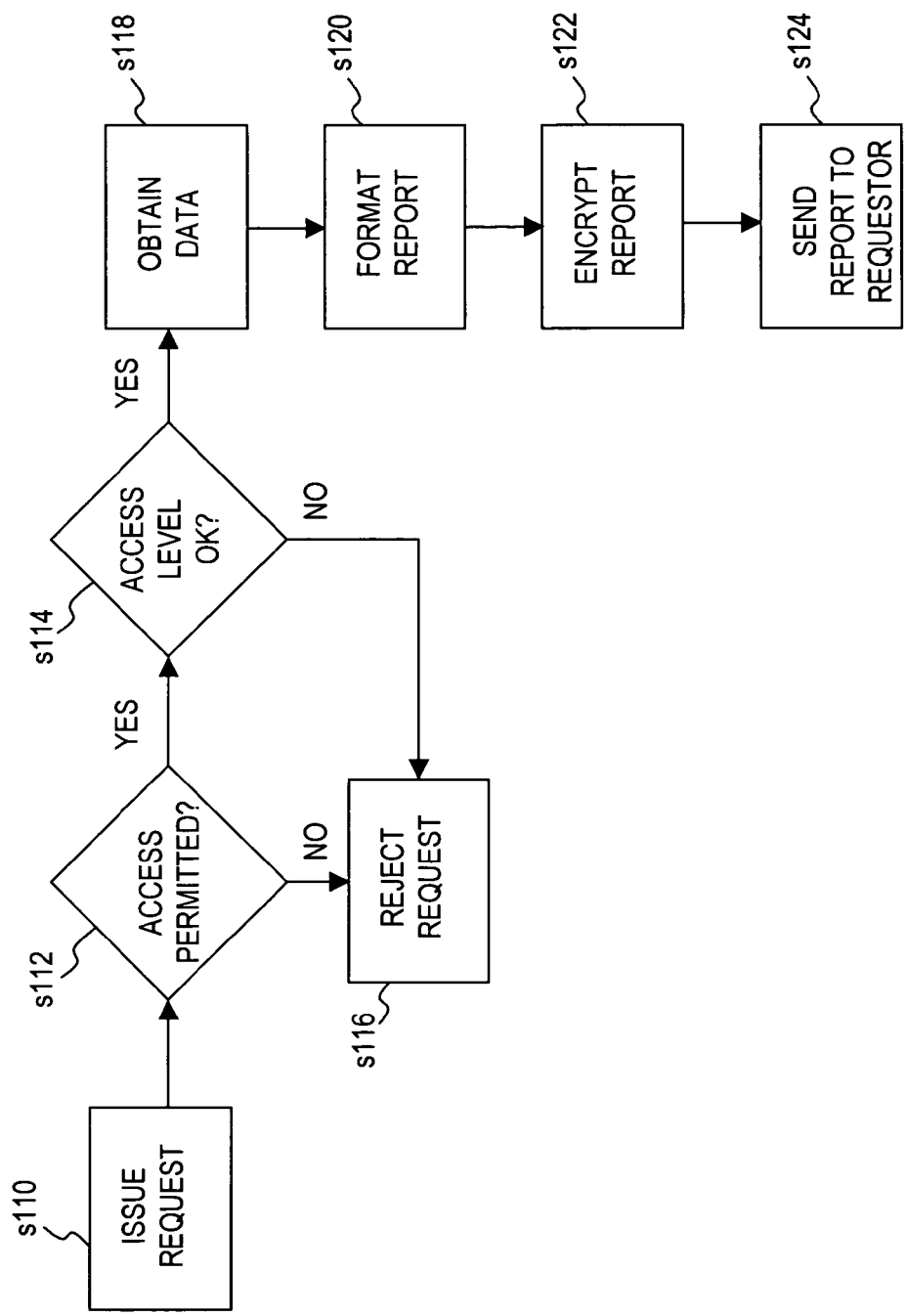
FIG. 5 is a flow diagram of a process for obtaining reports according to an embodiment of the present invention.

Referring now to FIG. 5 in combination with FIGS. 3 and 4, in operation any requestor may at step s110 request a report from processing center 20 pertaining to the stored pharmacy data. The requestor may issue the request to processing center 20 via electronic communications network 30. Upon receipt of the request, access screen 40 checks the credentials of the requestor for authority at step s112. If the requestor's credentials do not meet a predetermined set of criteria, the request is rejected and the requestor may receive at step s116 a reply via communications portion 45 and electronic communications network 30 denying the request. If the requestor has permission to access stored data, the request is passed to security level screen 80 at step s114, wherein the data request and the credentials of the requester are checked to ensure that the request does not exceed an approved level of privileges according to a predetermined hierarchy or arrangement. An example access violation would be personnel at a pharmacy 12 attempting to obtain reports pertaining to another pharmacy. If the request violates the approved level of access, the requestor may receive at step s116 a reply via communications portion 45 and electronic communications network 30 denying the request. If the request falls within the scope of allowed access for the particular requester, the data requested is obtained at step s118 from the data warehouse 50 and/or data mart 70, and is formatted via formatting portion 100 at step s120 to a pre-determined format. The report may optionally be encrypted via an encryption method 105 at step s122. The formatted report, which may be based on current and/or historical data, is then sent to the requestor at step s124, via network 30.

While this invention has been shown and described with respect to a detailed embodiment thereof, it will be understood by those skilled in the art that various changes in form and detail thereof may be made without departing from the scope of the claims of the invention. One skilled in the art will recognize that many of the separately-described functions of the various embodiments of the present invention may be combined or rearranged to accomplish the desired result. For example, referring to FIGS. 3 and 4, data mart 70 may be a physical subset of data warehouse 50. Further, any desired combination of access security level function 40, security level screening function 80, report formatting function 90, decryption function 100 and encryption function 105 may be embodied as portions of one or more computer programs residing on a computer system (not shown) associated with processing center 20 to accomplish the desired results of the processing center. These examples are for illustrative purposes only and are not intended to be limiting with regard to the arrangement or combination of the components of the present invention.

What is claimed is:

1. A method for storing and reporting pharmacy data, comprising the steps of:

generating by a plurality of pharmacies, each of the pharmacies operating within a managed care organization, electronic pharmacy data comprising medical, financial and transactional information related to pharmaceutical transactions;

receiving over a network, by a processing center of the managed care organization, a data transfer request to transfer respective electronic pharmacy data from at least one of the plurality of pharmacies;

providing first access security by the processing center in response to the data transfer request, wherein the first access security includes checking credentials defined by the processing center and submitted for authorization by the at least one pharmacy;

providing second access security by the processing center in case the at least one pharmacy passes the first access security, wherein the second access security includes, prior to accepting the respective electronic pharmacy data by the processing center, checking whether the respective electronic pharmacy data meet at least one predefined validity requirement defined by the processing center;

receiving, by the processing center, a transfer of the respective electronic pharmacy data pursuant to compliance with the second access security;

processing, organizing and structuring the electronic pharmacy data by the processing center to format the electronic pharmacy data in accordance with at least one of a predetermined protocol and format;

storing the processed electronic pharmacy data in a data warehouse;

storing subsets of the processed electronic pharmacy data in a data mart, the subsets being adapted to meet specific demands of particular requestors in terms of analysis, content, presentation and format, by storing a portion of a larger set of data residing in the data warehouse thereby to allow preparation of predetermined sets of reports pertinent to the particular requestors;

receiving by the processing center a data request from a data requestor to obtain at least a portion of the processed electronic pharmacy data, the data requestor having a privilege level identifying the type of data available to the requestor;

providing third access security by the processing center in response to the data request, wherein the third access security includes checking credentials defined by the processing center and submitted for authorization by the data requestor ;

providing fourth access security by the processing center in case the data requestor passes the third access security, wherein the fourth access security includes checking whether requested electronic pharmacy data is consistent with the scope of the privilege level of the data requestor;

formatting the portion of the electronic pharmacy data requested by the data requestor into a report pursuant to compliance with the fourth access security, the portion of the electronic pharmacy data for the report being developed from the data in the data warehouse or the subsets of the data in the data mart; and providing the report to the requestor.

2. The method of claim 1, further comprising the steps of:
encrypting by the respective plurality of pharmacies the pharmacy data before it transferring the electronic pharmacy data to the processing center; and
decrypting the electronic pharmacy data by the processing center after the electronic pharmacy data is received.

3. The method of claim 1 wherein the electronic pharmacy data are received via an electronic communications network.

4. The method of claim 3, wherein the requestor requests and receives the report by means of an electronic communications network.

5. The method of claim 4 wherein the electronic communications network is an intranet.

6. The method of claim 4 wherein the electronic communications network is the internet.

7. The method of claim 1, wherein the requestor is selectively allowed access to a greater or lesser portion of the electronic pharmacy data based upon predetermined criteria.

8. The method of claim 1, further comprising the step of checking by the processing center the electronic pharmacy data for defects before storing it.

9. The method of claim 1, further comprising the step of encrypting the report by the processing center before sending it to the requestor.

10. The method of claim 1, wherein the report represents financial performance by an individual pharmacy, financial performance by a plurality of pharmacies, or a medication review.

11. The method of claim 1, wherein the processing center formats the electronic pharmacy data or the report to comply with HIPAA.

* * * * *